US005728282A

United States Patent [19]
Bashkin et al.

[11] Patent Number: 5,728,282
[45] Date of Patent: Mar. 17, 1998

[54] DENATURING SEPARATION MATRIX HAVING HYDROXYETHYL CELLULOSE FOR NUCLEIC ACID ELECTROPHORESIS

[75] Inventors: John S. Bashkin, Mountain View; David L. Barker, Foster City; Richard F. Johnston, Murphys, all of Calif.

[73] Assignee: Molecular Dynamics, Sunnyvale, Calif.

[21] Appl. No.: 631,353

[22] Filed: Apr. 12, 1996

Related U.S. Application Data

[62] Division of Ser. No. 500,097, Jul. 10, 1995, Pat. No. 5,534,123.

[51] Int. Cl.$^6$ .......................... G01N 27/26; G01N 27/447
[52] U.S. Cl. .......................... 204/455; 204/451; 204/454; 204/601; 204/605
[58] Field of Search .......................... 204/601, 602, 603, 604, 605, 451, 452, 453, 454, 455

[56] References Cited

U.S. PATENT DOCUMENTS

| | | | |
|---|---|---|---|
| 4,810,183 | 3/1989 | Place et al. | 425/434 |
| 5,008,196 | 4/1991 | Connolly et al. | 435/240.2 |
| 5,089,111 | 2/1992 | Zhu et al. | 204/180.1 |
| 5,110,424 | 5/1992 | Chin | 204/180.1 |
| 5,126,021 | 6/1992 | Grossman | 204/180.1 |
| 5,164,055 | 11/1992 | Dubrow | 204/180.1 |
| 5,332,481 | 7/1994 | Guttman | 204/182.8 |
| 5,374,527 | 12/1994 | Grossman | 435/6 |
| 5,567,292 | 10/1996 | Madabhushi et al. | 204/451 |

FOREIGN PATENT DOCUMENTS

| | | |
|---|---|---|
| WO91/11709 | 8/1991 | WIPO . |
| WO94/03643 | 2/1994 | WIPO . |

OTHER PUBLICATIONS

Ram P. Singhal and Jun Xian, "Separation of DNA restriction fragments by polymer–solution capillary zone electrophoresis Influence of polymer concentration and ion–pairing reagents" Journal of Chromatography A, 652 (1993) no month available 47–56.

Barron, Annelise E. et al., "Capillary electrophoresis of DNA in uncross–linked polymer solutions," *Journal of Chromatography A*, 652 (1993), pp. 3–16. no month available.

Clark, Steven M. et al., "High–Speed Parallel Separation of DNA Restriction Fragments Using Capillary Array Electrophoresis," *Bioanalytical Biochemistry*, 215 (1993) no month available, pp. 163–170.

Grossman, Paul D. et al., "Capillary electrophoresis of DNA in entangled polymer solutions," *Journal of Chromatography*, 559 (1991), pp. 257–266. no month available.

Grossman, Paul D., "Electrophoretic separation of DNA sequencing extension products using low–viscosity entangled polymer networks," *Journal of Chromatography A*, 663 (1994), no month available pp. 219–227.

Heller, Christoph et al., "Brief Report: Electrophoretic separation of oligonucleotides in replenishable polyacrylamide–filled capillaries," *Applied and Theoretical Electrophoresis*, 4 (1994) no month available pp. 39–41.

Hjertén, Stellan, "High–Performance Electrophoresis Elimination of Electroendosmosis and Solute Adsorption," *Journal of Chromatography*, 347 (1985) no month available, pp. 191–198.

Huang, Xiaohua C. et al., "DNA Sequencing Using Capillary Array Electrophoresis," *Anal. Chem.*, 64 (1992) no month available, pp. 2149–2154.

Kleemiss, Maria H. et al., "Capillary electrophoresis of DNA restriction fragments with solutions of entangled polymers," *Electrophoresis*, 14 (1993) no month available, pp. 515–522.

Mathies, Richard A. et al., "Capillary array electrophoresis: an approach to high–speed, high–throughput DNA sequencing," *Nature*, vol. 359, Sep. 10, 1992, pp. 167–169.

Rocheleau, Marie J. et al., "Formamide modified polyacrylamide gels for DNA sequencing by capillary gel electrophoresis," *Electrophoresis*, 13 (1992) no month available, pp. 484–486.

Ruiz–Martinez, Marie C. et al., "DNA Sequencing by Capillary Electrophoresis with Replaceable Linear Polyacrylamide and Laser–Induced Fluorescence Detection," *Anal. Chem.*, 65 (1993) no month available, pp. 2851–2858.

Singhal, Ram P. et al., "Separation of DNA restriction fragments by polymer–solution capillary zone electrophoresis; influence of polymer concentration and ion–pairing reagents," *Journal of Chromatography A*, 652 (1993) no month available, pp. 47–56.

Nishigaki, Koichi et al., "Structural Analysis of Nucleic Acids by Precise Denaturing Gradient Gel Electrophoresis: I. Methodology," *J. Biochem.*, 111 (no month available 1992), pp. 144–150.

"High–resolution capillary electrophoretic analysis of DNA in free solution," *Electrophoresis*, 13 (no month available 1992), pp. 18–31.

*Primary Examiner*—Kathryn L. Gorgos
*Assistant Examiner*—John S. Starsiak, Jr.
*Attorney, Agent, or Firm*—Thomas Schneck; George B. F. Yee

[57] ABSTRACT

A capillary electrophoresis separation matrix for single-stranded nucleic acids, along with methods for using and preparing the matrix, are disclosed. The separation matrix provides denaturing conditions and contains hydroxyethyl cellulose (HEC) in combination with urea, and preferably also includes formamide. The separation matrix may be used for DNA sizing and sequencing applications and provides a single-base resolution to approximately 500 base pairs. The separation matrix is inexpensive, easy to prepare, requires no polymerization steps, and is of low enough viscosity to be pumped easily into and out of capillary tubes for electrophoresis. The low viscosity allows for high throughput of samples and reuse of the capillary tubes for numerous separations.

9 Claims, 2 Drawing Sheets

DENATURING SEPARATION MATRIX HAVING HYDROXYETHYL CELLULOSE FOR NUCLEIC ACID ELECTROPHORESIS

This is a divisional of application Ser. No. 08/500,097 filed on Jul. 10, 1995 now U.S. Pat. No. 5,534,123.

TECHNICAL FIELD

The present invention relates to separation matrices for capillary electrophoresis, and more particularly to separation matrices which may be used for DNA sequencing.

BACKGROUND ART

Capillary electrophoresis (CE) is a powerful tool for rapid high resolution separations of nucleic acids. CE has been used for separation of both double-stranded DNA, as in some restriction fragment applications, and single-stranded DNA, as in DNA sequencing and other fragment sizing applications.

Most CE analysis of DNA is carried out with polyacrylamide as the main component of the support or matrix within which the samples are separated. Polyacrylamide is well-suited to CE nucleic acid fragment separations because of its high resolution capabilities. For example, see U.S. Pat. No. 5,374,527 and 5,126,021 to Grossman and U.S. Pat. No. 5,164,055 to Dubrow. As suggested in the Grossman '527 patent, however, rapid loading and reloading of materials into a capillary tube represents a significant aim in the improvement of CE. This is difficult to achieve with most forms of polyacrylamide due to their high viscosity. Currently, capillary tubes are generally discarded after a CE run in polyacrylamide.

Other difficulties with the use of polyacrylamide include the time and careful control required for polymerization and generation of appropriate polymer molecular weight distributions. In addition, air bubbles that may form within the narrow-bored capillary tubes during the acrylamide polymerization process may interfere with the separation of samples.

CE equipment, and particularly automated CE equipment, would benefit greatly from a separation matrix that may quickly and easily be prepared and introduced into the capillary tube and provide high resolution of the nucleic acid samples. It would also be advantageous to have a separation matrix which can easily be removed from the capillary tube, thus allowing a capillary tube to be reused many times by the addition of a new separation matrix for each electrophoretic run, and which avoids the use of acrylamide, a known neurological toxin.

DISCLOSURE OF THE INVENTION

The above objects have been achieved with a denaturing separation matrix for electrophoresis of nucleic acid molecules, and methods for making and using the separation matrix to achieve rapid, high resolution separations. The separation matrix contains hydroxyethyl cellulose (HEC) in combination with urea. Additionally, the separation matrix may comprise formamide.

The HEC is present in a concentration of 1 to 3% w/v, but preferably 2% w/v, of the separation matrix. The urea is present in a concentration of 5 to 7M, but preferably 6M. The formamide, when present, is in a range of less than or equal to 30% v/v of the separation matrix, but is preferably present in a concentration of 10% v/v. The HEC, urea, and formamide are prepared in an aqueous solution, preferably 1×TBE.

The separation matrix of the present invention is appropriate for nucleic acid sequencing and fragment sizing applications in CE, or other applications requiring separations of nucleic acids in single-stranded form. The HEC and urea matrix provides denaturing conditions, necessary for sequencing applications, and allows for nucleic acid Separations with high resolution. A Length-of-Read (LOR) of approximately 500 or more base pairs is equivalent to the LOR achieved with polyacrylamide matrices. The LOR is the point at which the peak spacing equals the peak width in a plot of peak spacing and peak width as a function of base number. Preparation of the separation matrix is preferably achieved by initially subjecting an aqueous solution of HEC to an ion-exchange resin to remove charged impurities. This step contributes to the high resolution achieved with the separation matrix. The formamide also serves as a denaturant, helping to reduce compressions within the nucleic acid strands, and to reduce the viscosity of the separation matrix. The relatively low viscosity of the separation matrix contributes to the ease with which it may be manipulated in CE applications.

The separation matrix is easy to prepare with commercially available, non-toxic HEC. It requires no polymerization and is of sufficiently low viscosity to be easily introduced and removed from capillary electrophoresis tubes. The separation matrix of the present invention is especially well-suited to capillary array electrophoresis. Replaceable gel matrices are beneficial for many DNA applications because they are cost-effective and allow for a high throughput of samples.

ACE separation matrix incorporating HEC as a base material and providing denaturing conditions, especially for high resolution sequencing of DNA fragments, was previously not believed to be workable, because of the relatively simple nature of the HEC molecule as compared with the complex entanglement network formed by polyacrylamide. The present invention thus represents an important advance in the fields of CE and DNA sequencing.

BEST MODE FOR CARRYING OUT THE INVENTION

Figure 1:
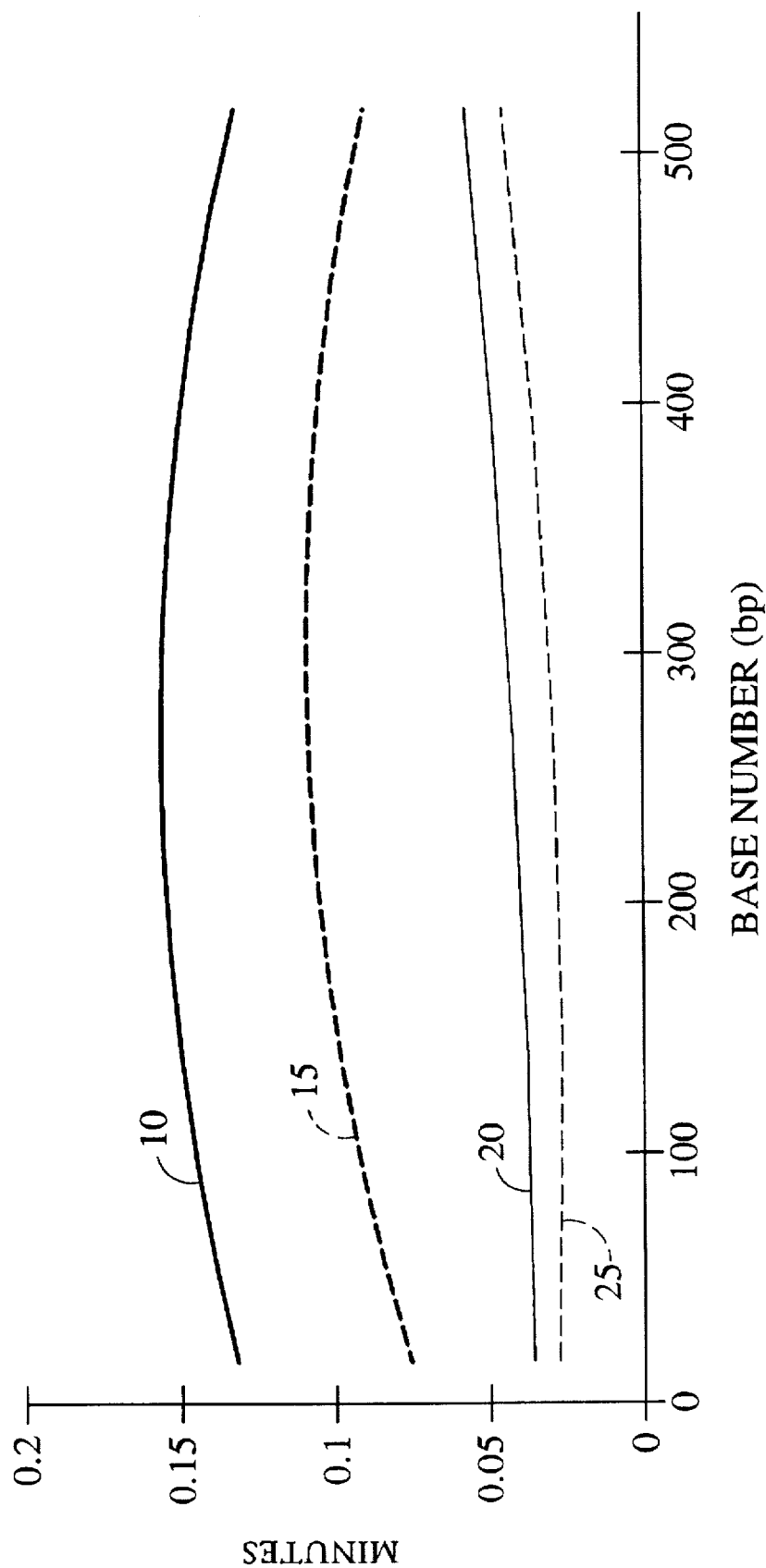
FIG. 1 is a graphical representation of peak spacings and peak widths versus base number for the separation matrix of the present invention and a prior art matrix.

The preferred embodiment of the separation matrix of the present invention contains 2% w/v HEC, 6M urea, and 10% v/v formamide in a solution of 1×TBE. The HEC may be present in a concentration of 1–3% w/v, but 2% is optimum. The urea may be present in a concentration of 5–7M, but 6M is preferred. The formamide, when it is present in the separation matrix, is in a concentration of less than or equal to 30% v/v, but is preferably present in a concentration of 10% v/v. A 1×TBE solution preferably serves as the aqueous solution in which the HEC and urea are dissolved, and the formamide is dispersed. 1×TBE, or Tris-boric acid EDTA, is a well-known buffer in the field of molecular biology. It is used in experiments involving nulceic acids and generally comprises 89–90 mM Tris, 89–90 mM boric acid, and 2–5 mM EDTA (ethylenediamine tetraacetic acid) at pH 8.0–8.3. The 1×TBE used by the present inventors comprised 89 mM Tris, 89 mM boric acid, and 2 mM EDTA at a pH of 8.0.

Other buffers, such as TBE ranging in concentration from 0.5×–2×, or TE, or TAE, may also be used, but may require optimization of pH and other run conditions for electrophoresis.

Since oxidized forms of cellulose or other charged impurities may affect electrophoresis, the HEC is preferably purified by treatment with an ion-exchange resin which leaves the HEC substantially free of charged impurities. The HEC from different sources may vary in purity, porosity, and molecular weight, so different purification schemes may be necessary. The preferred HEC of the present invention was obtained from Polysciences in Warrington, Pa. and has a molecular weight of 90,000–105,000 daltons.

The separation matrix of the present invention is typically prepared by first creating a solution of HEC and urea and purifying this solution. The first step is dissolving HEC and urea in water to produce a concentration of greater than 2% w/v of HEC and a concentration of greater than 6M of the urea. If concentrations of these two components are desired at the high end of their respective concentration ranges, then it is understood to adjust the concentrations of this first solution, for example to produce a first solution having a greater than 3% w/v concentration of HEC and a concentration of greater than 7M of urea. The HEC/urea solution is typically purified by contact with an ion-exchange resin. The ion-exchange resin should be a mixed bed strong ion-exchanger having both acidic and basic gel types. Amberlite MB-1 ion-exchange resin, available from Mallinkrodt of Paris, Ky., was used by the present inventors. Thus, a 50 ml batch of this first solution was prepared by dissolving 1.25 g HEC and 22.5 g urea in water. This solution was stirred overnight with 0.5 g Amberlite.

After purification of the HEC/urea solution by contact with the ion-exchange resin, the resin and the solution are separated, as by centrifugation. Typically, 30 minutes in a standard table-top centrifuge is sufficient. The supernatant that results comprises the purified HEC/urea solution. This supernatant is removed from the pelleted resin.

Tris, boric acid, and EDTA, preferably in the form of concentrated TBE, and, if desired, formamide are added to a portion of the purified HEC/urea solution and the solution is diluted, if necessary, to produce a separation matrix having a final concentration of 2% w/v HEC, 6M urea, 1×TBE, and 10% v/v formamide. It is understood that adjustments to the portions and dilutions may be made to produce a separation matrix having components with other concentrations within the ranges specified.

When formamide is desired in the separation matrix, it may be added to the purified HEC/urea solution, as described above, or it may be incorporated into the original solution of HEC and urea, before the solution is purified by contact with the ion-exchange resin. If it is added to the solution prior to the purification step, then it may be necessary to create a greater than desired concentration, so that the final concentration of the formamide, after any necessary dilutions in the preparation of the separation matrix, is the desired concentration. For example, a concentration of at least 10% v/v formamide in the pre-purified solution of HEC and urea will enable preparation of a final separation matrix with a concentration of 10% v/v formamide. Formamide is useful in untangling compressions in the nucleic acid strands, which occur in areas of high guanine-cytosine nucleotide concentrations, and which may cause anomalous electrophoretic runs if left untreated. Formamide also contributes to the low viscosity of the separation matrix.

The separation matrix is then stirred for approximately 30 minutes followed by degassing under vacuum for approximately one hour. For further removal of air bubbles and impurities, the separation matrix may be centrifuged, as in microcentrifuge tubes, for 10 minutes at approximately 14,000 rpm. The resulting supernatant may then be used for filling of capillary tubes and subsequent electrophoresis. Removal of air and impurities from the separation matrix is critical in the narrow-bore context of CE applications.

The separation matrix may also be made in some other manner. For example, a 2% w/v solution of HEC and 6 or 7M solution of urea may be created directly in 1×TBE buffer at pH 8.0. HEC and urea are dissolved overnight in the 1×TBE, and the solution may be filtered for purification. Degassing and centrifugation of the solution, as before, may be performed before introduction of the matrix into the capillary tube for electrophoresis. Considerations such as the difficulty of preparing high concentrations of urea solutions and the relative viscosity of HEC in solution should be taken into account, however, if an alternate method is used for preparation of the separation matrix.

Once the separation matrix is prepared, a portion of it is introduced into a capillary tube, as with pressure of 400 psi. The filling process is typically completed in less than two minutes. The separation matrix of the present invention is used for CE as both the gel matrix and the run buffer for each electrode. After the filling process is complete, a pre-run is usually done for about 10 minutes at 12 kV, prior to introduction of the sample. This pre-run serves to stabilize the current. The sample is introduced at an entrance end of the capillary tube, e.g. by electrokinetic injection, and the well-known separation process of electrophoresis is performed.

It is advantageous in the CE of nucleic acids to treat the inside wall of the capillary tube with a layer of polyacrylamide, as taught by Stellan Hjertén, in "High-Performance Electrophoresis Elimination of Electroendosmosis and Solute Adsorption," *Journal of Chromatography*, 347 (1985), pages 191–198. In the method of using the separation matrix of the present invention, it is therefore preferred that the inside wall of the capillary tube be coated with polyacrylamide prior to filling of the tube with a portion of the prepared separation matrix, for best performance.

In the prior art, the use of high viscosity polyacrylamide generally required that the capillary tube and the matrix be discarded after the separation had occurred and data collected. The present invention represents an improvement, however, because the separation matrix is of sufficiently low viscosity to be easily and cleanly removed from the capillary tube.

Generally, after completion of an electrophoretic run, water is run through the capillary tube under nitrogen pressure at 400 psi, until the capillary tube is rinsed clean, which takes approximately 5 minutes. The capillary tube is then rinsed with methanol and dried under a flow of nitrogen. The capillary tube is then ready for filling with a new portion of the separation matrix. In this way, capillary tubes may be reused many times. Turn-around time between electrophoretic runs is currently approximately 15 minutes, but may be shortened with automation.

A CE instrument having an array of capillary tubes is typically used for processing of numerous nucleic acid samples. See Richard A. Mathies and Xiaohua C. Huang, "Capillary array electrophoresis: an approach to high-speed, high-throughput DNA sequencing," *Nature*, Vol. 359, Sep. 10, 1992, pages 167–169. For example, a 48 capillary tube array in an electrophoresis apparatus allows simultaneous filling of 48 capillary tubes with the separation matrix. This arrangement corresponds conveniently to half of a standard microtiter plate. The nucleic acid samples are then each introduced to an individual capillary tube at its entrance end. Then, the electrophoretic separations are simultaneously performed on all capillary tubes of the array having samples. Cleaning of the capillary tubes for further sample separations may also occur in all tubes simultaneously. This array system allows for high throughput of nucleic acid samples. The separation matrix of the present invention contributes significantly to the usage of such an apparatus since the matrix is easily replaceable, both because of its low viscosity which allows for rapid filling and cleaning of the capillary tubes, and because the separation matrix is inexpensive and convenient to use.

Because no polymerization is necessary with the separation matrix of the present invention, there is no delay between the time of filling the capillary tube with the matrix and the time of using the separation matrix for an electrophoretic run. The pre-run before introduction of the sample is a standard step in capillary electrophoresis systems having a variety of matrices, and is usually done to equilibrate the electrophoretic system and to standardize the electrophoretic runs of various samples. Electrophoresis is usually performed at room temperature for sequencing and sizing applications of nucleic acids.

FIG. 1 presents a plot of peak spacings and peak widths as a function of base number for an M13mp18 ddT sequencing reaction (1 µg DNA, 15 second injection at 12 kV, run at 12 kV), electrophoresed with the separation matrix of the present invention, shown in solid lines, and with a cross-linked polyacrylamide (3%T/3%C) of the prior art, shown in dotted lines. Line 10 represents peak spacing and line 20 represents peak width of the HEC/urea/formamide separation matrix. Line 15 and line 25 represent the peak spacing and peak width, respectively, of the prior art matrix. FIG. 1 illustrates the trend of both the present invention and the prior art matrix to provide an LOR of between 500 to 600 base pairs.

Figure 2:
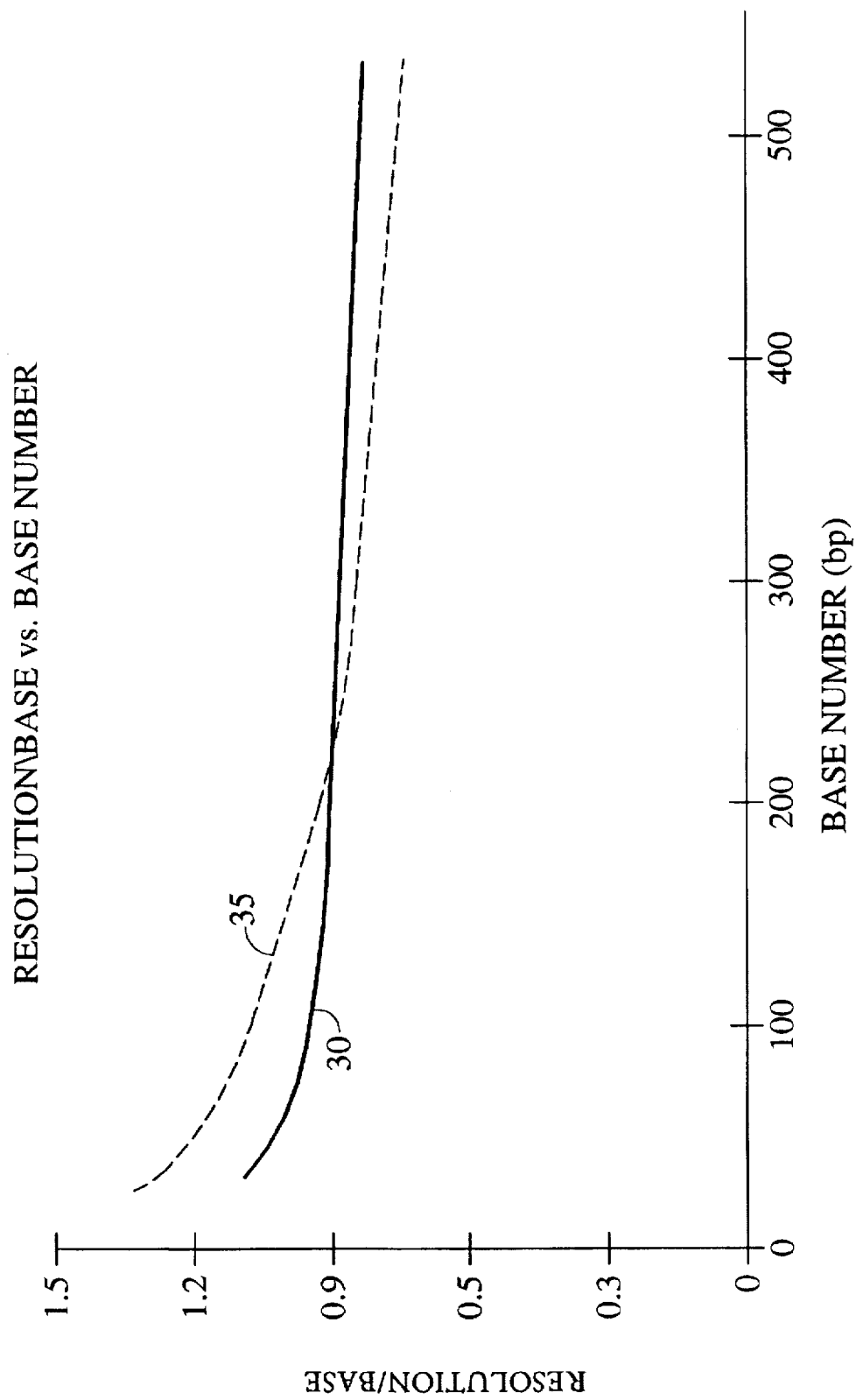
FIG. 2 is a graphical representation of resolution/base versus base number for the separation matrix of the present invention and a prior art separation matrix.

The resolution of the separation matrix of the present invention is comparable to that of polyacrylamide matrices, as well, as seen in FIG. 2. FIG. 2 presents the resolution per base versus base number, for the present invention, shown by solid line 30, and a cross-linked polyacrylamide matrix (3%T/3%C) of the prior art, shown by dotted line 35. The resolution is defined as taught in Paul D. Grossman, "Electrophoretic separation of DNA sequencing extension products using low-viscosity entangled polymer networks," *Journal of Chromatography A*, 663 (1994), pages 219–227.

The urea of the separation matrix is a powerful denaturant which causes nucleic acids to run through the capillary tube in single-stranded form. The samples which are loaded into the capillary tube are generally single-stranded, as in the case of DNA sequencing reaction mixtures, but may be in double-stranded form. The latter samples would become single-stranded during the electrophoretic run.

Although capillary electrophoresis of nucleic acids has been emphasized, the present invention may be applicable to other separations that are required to occur under denaturing conditions.

We claim:

1. A method for rapid separation of a plurality of nucleic acid samples, comprising:

(a) providing a denaturing separation matrix having at least 1% w/v hydroxyethyl cellulose and at least 5M urea in an aqueous solution, (b) providing an array of capillary tubes including covalently modifying the inside wall of each of the capillary tubes with polyacrylamide prior to filling the capillary tubes with the separation matrix, (c) filling each capillary tube of the array with a portion of the separation matrix, (d) introducing one of the nucleic acid samples to an entrance end of each of the capillary tubes of the array, and (e) separating the samples which are at the entrance ends of the capillary tubes by electrophoresis.

2. The method of claim 1 further comprising:

(f) removing the portion of the separation matrix from each of the capillary tubes of the array, (g) cleaning each of the capillary tubes of the array, and (h) repeating steps (c)–(e) for any remaining nucleic acid samples.

3. The method of claim 1 wherein the step of providing a separation matrix further comprises providing a separation matrix having formamide in combination with the hydroxyethyl cellulose and the urea.

4. The method of claim 1 wherein the step of providing a separation matrix further comprises providing a separation matrix having TBE as the aqueous solution.

5. In a method of resolving a nucleic acid sequencing reaction mixture, the improvement comprising:

electrophoresing the mixture in a separation matrix-filled capillary tube, the separation matrix including at least 1% w/v hydroxyethyl cellulose, at least 5M urea in an aqueous solution, and formamide, wherein the inside wall of the capillary tube is covalently modified with polyacrylamide prior to filling the capillary tube with the separation matrix.

6. In the method of claim 5, the improvement wherein the aqueous solution is tris-borate and EDTA (TBE).

7. In a method of resolving a nucleic acid sequencing reaction mixture, the improvement comprising:

providing a capillary tube;

covalently modifying the inside wall of the capillary tube with polyacrylamide prior to filling the capillary tube with a separation matrix;

filling the capillary tube with a separation matrix, the separation matrix including at least 1% w/v hydroxyethyl cellulose and at least 5M urea in an aqueous solution; and electrophoresing the mixture in the separation matrix-filled capillary tube.

8. In the method of claim 7, the improvement further comprising:

including formamide in the separation matrix.

9. In the method of claim 7, the improvement wherein the aqueous solution is tris-borate and EDTA (TBE).

* * * * *